US011115539B2

(12) United States Patent
Yang et al.

(10) Patent No.: US 11,115,539 B2
(45) Date of Patent: Sep. 7, 2021

(54) SMART VOICE SYSTEM, METHOD OF ADJUSTING OUTPUT VOICE AND COMPUTER READABLE MEMORY MEDIUM

(71) Applicant: Unlimiter MFA Co., Ltd., Eden Island (SC)

(72) Inventors: Kuo-Ping Yang, Taipei (TW); Chih-Long Chang, Taipei (TW); Neo Bob Chih-Yung Young, Taipei (TW)

(73) Assignee: PIXART IMAGING INC., Hsin-Chu County (TW)

( * ) Notice: Subject to any disclaimer, the term of this patent is extended or adjusted under 35 U.S.C. 154(b) by 295 days.

(21) Appl. No.: 15/823,678

(22) Filed: Nov. 28, 2017

(65) Prior Publication Data
US 2018/0316795 A1    Nov. 1, 2018

(30) Foreign Application Priority Data
Apr. 28, 2017 (TW) .................................. 106114384

(51) Int. Cl.
*H04M 3/533* (2006.01)
*A61B 5/12* (2006.01)
(Continued)

(52) U.S. Cl.
CPC ......... *H04M 3/53375* (2013.01); *A61B 5/002* (2013.01); *A61B 5/0022* (2013.01); *A61B 5/121* (2013.01); *A61B 5/123* (2013.01); *A61B 5/7264* (2013.01); *A61B 5/749* (2013.01); *G06F 3/167* (2013.01); *G10L 13/02* (2013.01); *G10L 15/1815* (2013.01); *H04M 3/53333* (2013.01); *H04M 3/53341* (2013.01);
(Continued)

(58) Field of Classification Search
CPC .... H04R 1/1016; H04R 3/04; H04R 2225/41; H04R 2430/01; G06F 3/167; G06F 40/30; G10L 15/26; G10L 13/02; G10L 15/1815; H04M 1/6066; H04M 3/53375; H04M 3/53341; H04M 3/53333; H04M 3/4936; A61B 5/7264; A61B 5/749; A61B 5/002; A61B 5/0022; A61B 5/123; A61B 5/121; A61B 5/0004; G16H 40/67; G16H 50/20
See application file for complete search history.

(56) References Cited

U.S. PATENT DOCUMENTS 8,447,285 B1 * 5/2013 Bladon ............. H04M 3/53341
455/414.4
8,781,836 B2 * 7/2014 Foo ..................... H04R 25/505
704/269

(Continued)

*Primary Examiner* — Lisa Hashem
(74) *Attorney, Agent, or Firm* — Bacon & Thomas, PLLC

(57) ABSTRACT

A smart voice system is disclosed. The smart voice system includes a data receiving module, a voice message receiving module, a voice response module and a voice message output module. The data receiving module receives a hearing evaluation data of a user, and acquiring a hearing parameter according to the hearing evaluation data. The voice message receiving module receives a voice message inputted by the user. The voice response module acquires a response voice message corresponding to the voice message and the frequency of the response voice message is adjusted according to the hearing parameter. The voice message output module outputs the response voice message.

9 Claims, 6 Drawing Sheets

(51) Int. Cl.

| | | |
|---|---|---|
| *G10L 13/02* | (2013.01) | |
| *H04R 3/04* | (2006.01) | |
| *G10L 15/18* | (2013.01) | |
| *G06F 3/16* | (2006.01) | |
| *A61B 5/00* | (2006.01) | |
| *H04M 3/493* | (2006.01) | |
| *G06F 40/30* | (2020.01) | |

(52) U.S. Cl.
CPC .............. *H04R 3/04* (2013.01); *A61B 5/0004* (2013.01); *G06F 40/30* (2020.01); *H04M 3/4936* (2013.01); *H04R 2225/41* (2013.01); *H04R 2430/01* (2013.01)

(56) References Cited

U.S. PATENT DOCUMENTS

| | | | | |
|---|---|---|---|---|
| 9,901,736 | B2* | 2/2018 | Chen | G06F 40/58 |
| 10,192,552 | B2* | 1/2019 | Raitio | G10L 13/033 |
| 10,296,093 | B1* | 5/2019 | Christensen | G06F 3/016 |
| 10,303,715 | B2* | 5/2019 | Graham | G10L 15/22 |
| 2008/0031475 | A1* | 2/2008 | Goldstein | H04M 1/05 |
| | | | | 381/151 |
| 2010/0041447 | A1* | 2/2010 | Graylin | H04M 1/05 |
| | | | | 455/575.2 |
| 2015/0121215 | A1* | 4/2015 | Wohlert | G06F 9/453 |
| | | | | 715/706 |
| 2015/0278679 | A1* | 10/2015 | Sharma | H04L 63/101 |
| | | | | 706/11 |
| 2016/0118036 | A1* | 4/2016 | Cheatham, III | H04M 3/205 |
| | | | | 380/252 |
| 2017/0242653 | A1* | 8/2017 | Lang | H04W 8/24 |
| 2018/0146307 | A1* | 5/2018 | Petersen | H04R 25/552 |
| 2018/0182380 | A1* | 6/2018 | Fritz | G10L 15/22 |
| 2018/0270350 | A1* | 9/2018 | Engelke | H04M 1/2475 |
| 2019/0027131 | A1* | 1/2019 | Zajac, III | G10L 15/02 |
| 2019/0139542 | A1* | 5/2019 | Gunther | G06F 3/167 |
| 2019/0332680 | A1* | 10/2019 | Wang | G06F 17/289 |
| 2020/0189458 | A1* | 6/2020 | Akahori | B60Q 5/006 |
| 2020/0296510 | A1* | 9/2020 | Li | G06F 3/167 |
| 2020/0296534 | A1* | 9/2020 | Wang | H03G 5/165 |
| 2021/0152942 | A1* | 5/2021 | Bennett | H04R 5/00 |

* cited by examiner

| Gender Information | Age Information | Hearing Parameter |
|---|---|---|
| Male | 0~40 | 1010101010101010 |
| Female | 0~40 | 1010101010101010 |
| Male | 41~50 | 1010101020203030 |
| Female | 41~50 | 1010101010102020 |
| Male | 51~60 | 1010101020303040 |
| Female | 51~60 | 1010101010102030 |
| Male | 61~70 | 1010101020304040 |
| Female | 61~70 | 1010101010202030 |
| Male | 71~80 | 1010202040506060 |
| Female | 71~80 | 1010101010203040 |
| Male | 81~90 | 1010202040507070 |
| Female | 81~90 | 1010101020303040 |
| Male | 91~100 | 1010203050607070 |
| Female | 91~100 | 1010102030304050 |

FIG. 3

SMART VOICE SYSTEM, METHOD OF ADJUSTING OUTPUT VOICE AND COMPUTER READABLE MEMORY MEDIUM

BACKGROUND OF THE INVENTION

1. Field of the Invention

The present invention relates to a smart voice system and a method of adjusting output voice, particularly to a smart voice system that can output voice messages in a hearing state suitable for a user and a method of adjusting output voice.

2. Description of the Related Art

With the development of artificial intelligence technology, smart voice assistant has gradually developed and matured. The existing smart voice assistant with the use of large data and constantly updated has been able to answer a considerable number of human problems, and thus has gradually been widely used in daily life. However, the current smart voice assistant can produce different tones of voice according to different answer questions, but cannot adjust the sound frequency according to a user's hearing status. For the elderly or hearing impaired, there may be cases where the content of the reply cannot be heard or heard unclearly.

Therefore, it is necessary to devise a smart voice system that can adjust the sound output frequency to solve the problem in the prior art.

SUMMARY OF THE INVENTION

It is a major objective of the present invention to provide a voice service function that can output voice messages in a hearing state suitable for a user.

To achieve the above objective, the present invention discloses a smart voice system, which includes a data receiving module, a voice message receiving module, a voice response module, and a voice message output module. The data receiving module is used for receiving a user's hearing evaluation data, and acquiring a hearing parameter according to the hearing evaluation data, wherein the hearing parameter is the minimum volume data that the user can hear for different frequencies of sound. The voice message receiving module is used for receiving a voice message issued by the user. The voice response module is used for acquiring a response voice message adopted to reply to the voice message, wherein the frequency of the response voice message is adjusted according to the hearing parameter. The voice message output module is used for outputting the response voice message.

To achieve the above objective, the present invention further discloses a method of adjusting output voice applicable to a smart voice assistant, wherein the smart voice assistant is connected to the electronic device. The method of adjusting output voice in the present invention includes the following steps: receiving a user's hearing evaluation data, and acquiring a hearing parameter according to the hearing evaluation data, wherein the hearing parameter is the minimum volume data that the user can hear for different frequencies of sound; receiving a voice message issued by the user; analyzing the voice message, and searching for a response text message adapted to reply to the voice message based on the analysis result; generating a response voice message based on the response text message, wherein the frequency of the response voice message is adjusted according to the hearing parameter; and outputting the response voice message.

According to another embodiment of the present invention, the method of adjusting output voice is applicable to an electronic device, wherein the electronic device is connected a smart voice assistant. The method includes the following steps: receiving a user's hearing evaluation data, and acquiring a hearing parameter according to the hearing evaluation data, wherein the hearing parameter is the minimum volume data that the user can hear for different frequencies of sound; receiving a voice message issued by the user; sending the voice message to a smart voice assistant; receiving an original response voice message from the smart voice assistant, wherein the original response voice message is acquired by the smart voice assistant according to the voice message; adjusting the frequency of the original response voice message according to the hearing parameter to generate a response voice message; and outputting the response voice message.

The present invention further discloses a computer readable memory medium with a program by which the method of adjusting output voice disclosed in the present invention can be accomplished as the computer loads the program.

BRIEF DESCRIPTION OF THE DRAWINGS

FIG. 3 is a table showing the relationship of gender information, age information, and hearing parameters;

DETAILED DESCRIPTION OF THE PREFERRED EMBODIMENT

Hereafter, the technical content of the present invention will be better understood with reference to preferred embodiments.

Figure 1:
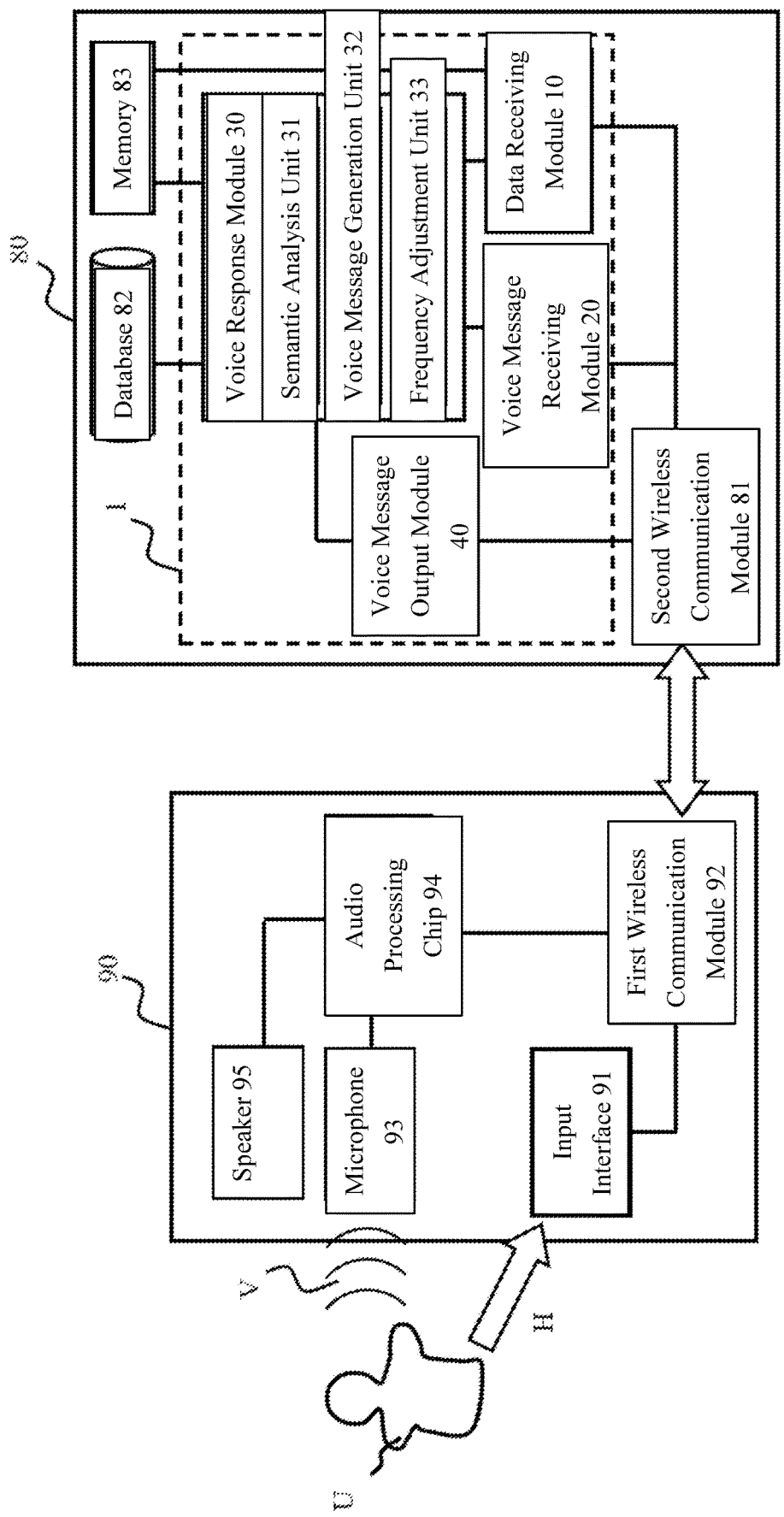
FIG. 1 is an architecture diagram of a smart voice system according to a first embodiment of the present invention.
Figure 4:
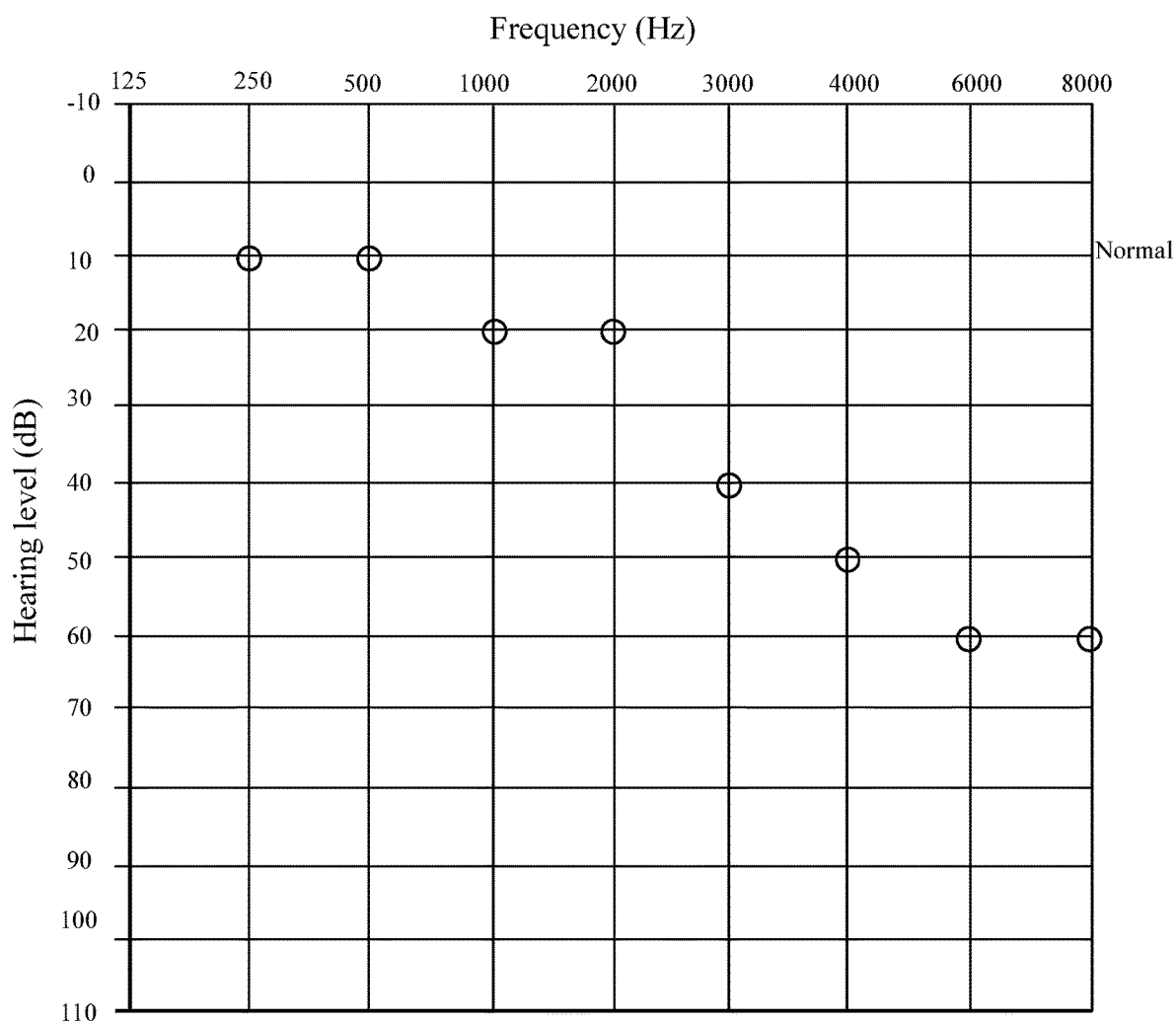
FIG. 4 is a graph showing hearing parameters.

Hereafter please first refer to FIG. 1, as well as FIGS. 3 and 4, wherein FIG. 1 is an architecture diagram of a smart voice system according to a first embodiment of the present invention; FIG. 3 is a table showing the relationship of gender information, age information, and hearing parameters; and FIG. 4 is a graph showing hearing parameters.

As shown in FIG. 1, in the first embodiment of the present invention, a smart voice system 1 is installed in a smart voice assistant 80. Besides the smart voice system 1, the smart voice assistant 80 also includes a second wireless communication module 81, database 82, and memory 83. The smart voice assistant 80 can be connected to an electronic device 90 through a second wireless communication module 81. Specifically, in the present embodiment, the electronic device 90 includes an input interface 91, a first wireless communication module 92, a microphone 93, an audio processing chip 94, and a speaker 95. The smart voice assistant 80 can be connected to the electronic device 90 through the communication of the second wireless communication module 81 and the first wireless communication module 92. In the embodiment of the present invention, the second wireless communication module 81 and the first wireless communication module 92 are wireless cards, but the present invention is not limited thereto.

The input interface 91, for example, may be a touch screen for the user U to input his/her hearing evaluation data H, such that the smart voice assistant 80 finds and acquires a corresponding hearing parameter according to the hearing evaluation data H (detailed hereafter). In the embodiment of the present invention, the hearing evaluation data H is age information and gender information of the user U, but the present invention is not limited thereto. The hearing evaluation data H can also be the data of the hearing parameter itself, and it is not necessary to include gender information.

The microphone 93 is used for receiving the voice message V issued by the user, i.e. receiving the voice issued by the user U.

The audio processing chip 94 is used for receiving the voice message V of the microphone 93 for analog/digital conversion processing to generate the digital format voice message V. Also, the voice message V in the digital format can be sent to the smart voice assistant 80 via the first wireless communication module 92.

The speaker 95 is used for processing the generated signal according to the audio processing chip 94 and playing the sound.

In the first embodiment of the present invention, the smart voice system 1 includes a data receiving module 10, a voice message receiving module 20, a voice response module 30, and a voice message output module 40. It should be noted that the above respective modules may not only be configured as hardware devices, software programs, firmware, or combinations thereof, but configured by circuit loop or other suitable types. Also, each of the modules can be configured individually or in the form of combination. In an embodiment, each module is stored in memory 83 and is executed by a processor (not shown) in the smart voice assistant 80 to implement the functions of the present invention. In another embodiment, each module can also be stored in a computer readable memory medium in a form of a software program. After the program is loaded and each module is implemented, the function of the present invention can be achieved. Additionally, the preferred embodiment of the present invention described here is only illustrative. To avoid redundancy, all the possible combinations of changes are not documented in detail. However, it shall be understood by those skilled in the art that each of the modules or elements described above may not be necessary. For the implementation of the present invention, the present invention may also contain other detailed, conventional modules or elements. Each module or component is likely to be omitted or modified depending on the needs. Other modules or elements may not necessarily exist between two of any modules.

In the first embodiment of the present invention, the data receiving module 10 is used for receiving a hearing evaluation data H from the electronic device 90. Specifically, in the present embodiment, after the electronic device 90 receives the hearing evaluation data H input by the user U via the input interface 91, the input hearing evaluation data H is sent to the smart voice assistant 80 through the first wireless communication module 92 and received by the data receiving module 10. In one of the embodiments, but not limited thereto, an input screen may be displayed on the display (not shown) of the electronic device 90 for the user U to input hearing evaluation data H; the hearing evaluation data H input to the input screen by the user U will be sent to the smart voice assistant 80. After receiving the hearing evaluation data H, the data receiving module 10 further acquires a hearing parameter according to the hearing evaluation data H, wherein the hearing parameter is the minimum volume data that the user can hear for different frequencies of sound. After acquiring the hearing parameter, the data receiving module 10 also stores the hearing parameter in the memory 83.

Figure 2:
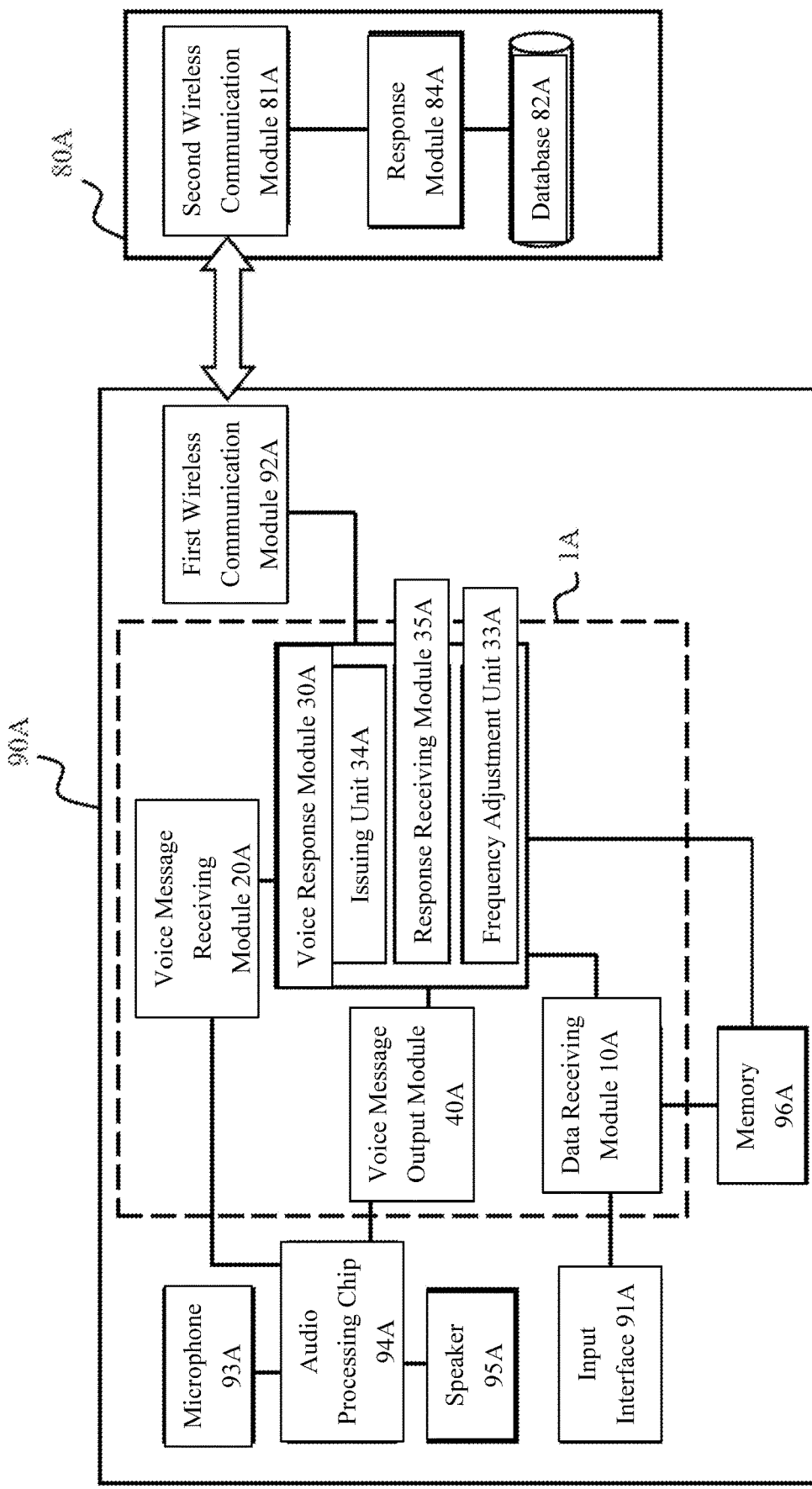
FIG. 2 is an architecture diagram of a smart voice system according to a second embodiment of the present invention.

Taking the relationship table shown in FIG. 3 as an example, once the age information and the gender information in the "hearing evaluation data H" are "71 to 80" and "male", the data receiving module 10 can find according to the relationship shown in FIG. 2 (which is stored in the database 82) that the user's hearing parameter is "1010202040506060", which can be represented by the graph shown in FIG. 4. As shown in FIG. 4, for user's sound of 250 and 500 Hz, the minimum volume that can be heard is 10 dB; for a sound of 1000 and 2000 Hz, the minimum volume that can be heard is 20 dB; for a sound of 3000 Hz, the minimum volume that can be heard is 40 dB; for a sound of 4000 Hz, the minimum volume that can be heard is 50 dB; for a sound of 6000 and 8000 Hz, the minimum volume that can be heard is 60 dB.

In the first embodiment of the present invention, the voice message receiving module 20 is used for received a voice message V issued by the user U. Specifically, in the present embodiment, after the voice (i.e. voice message V) issued by the user U is received by the microphone 93 and processed by an audio processing chip 94, it can be transmitted through the first wireless communication module 92 to the smart voice assistant 80, and can then be received by the voice message receiving module 20.

In the first embodiment of the present invention, the voice response module 30 is used for acquiring a response voice message adopted to reply to the voice message V, wherein the frequency of the response voice message is adjusted according to the aforementioned hearing parameter. In the present embodiment, the voice response module 30 includes a semantic analysis unit 31, a voice message generation unit 32, and a frequency adjustment unit 33. The semantic analysis unit 31 is used for analyzing a voice message V received from the voice message receiving module 20, and according to the analysis results to finding out a response text message adopted to reply to the voice message V according to the analysis results (the semantic analysis results and the relationship between the response text message are stored in the database 82). The voice message generation unit 32 is used for processing the response text message into an original response voice message. The semantic analysis of human speech and responding to the appropriate response based on the analysis results is the existing technology (e.g. Apple's Siri; also referring to the relevant technical literature of text-to-speech (TTS)), which is well known to those having the ordinary knowledge in the field of sound processing technology, and will not detailed hereafter. The frequency adjustment unit 33 is used for adjusting the frequency of the original response voice message according to the hearing parameter to generate the response voice message.

It should be noted here that in other embodiments, the aforementioned voice message generation unit 32 can also directly process the response text message into a response voice message according to a hearing parameter, that is, in the process of performing text-to-speech, the frequency of the output voice is adjusted according to the hearing parameter.

In the first embodiment of the present invention, the voice message output module 40 is used for outputting the response voice message to the second wireless communication module 81, and sending the response voice message to the electronic device 90 via the second wireless communication module 81. The response voice message, after the digital/analog conversion processing by the audio processing chip 94 of the electronic device 90, can be output by the speaker 95 (i.e. voice playback). Since the frequency of the response voice message is adjusted based on the hearing parameter associated with the hearing state of the user, the output of the voice can be suitable for users to listen.

Then, please refer to FIG. 2 which is an architecture diagram of a smart voice system according to the second embodiment of the present invention.

In the second embodiment of the present invention, a smart voice system 1A of the present invention is installed in the electronic device 90A. The electronic device 90A can be connected to a smart voice assistant 80A. The smart voice assistant 80A includes a second wireless communication module 81A, a database 82A, and a response module 84A. The smart voice assistant 80A can be communicated wirelessly with the electronic device 90A through the second wireless communication module 81A. Besides the smart voice system 1A, the electronic device 90A also includes an input interface 91A, a first wireless communication module 92A, a microphone 93A, an audio processing chip 94A, a speaker 95A, and memory 96A. Since the functions of these elements are the same as those of the first embodiment, they will not be detailed hereafter.

In the second embodiment of the present invention, the smart voice system 1A of the present invention includes a data receiving module 10A, a voice message receiving module 20A, a voice response module 30A, and a voice message output module 40A.

In the second embodiment of the present invention, the data receiving module 10A is used for receiving the hearing evaluation data H from the electronic device 90. Specifically, in the present embodiment, the hearing evaluation data H input by the user U via the input interface 91A will be transmitted to the smart voice system 1A, and received by the data receiving module 10A. After receiving the hearing evaluation data H, the data receiving module 10A further acquires a hearing parameter according to the hearing evaluation data H, wherein the hearing parameter is the minimum volume data that the user can hear for different frequencies of sound. After the hearing parameter is acquired, the data receiving module 10A stores the hearing parameter in the memory 96A.

In the second embodiment of the present invention, the voice message receiving module 20A is used for receiving a voice message V issued by the user U. Specifically, in the present embodiment, after the voice (i.e. voice message V) output by the user U is received by the microphone 93A and processed by the audio processing chip 94, it will be transmitted to the smart voice system 1A, and can then be received by the voice message receiving module 20A.

In the second embodiment of the present invention, the voice response module 30A is used for acquiring the response voice message adopted to reply to the voice message V, wherein the frequency of the response voice message is adjusted according to the hearing parameter described above. In the present embodiment, the voice response module 30A includes an issuing unit 34A, a response receiving unit 35A, and a frequency adjustment unit 33A. The issuing unit 34A is used for sending the received voice message to the smart voice assistant 80A through the first wireless communication module 92A. After the second wireless communication module 81A receives the voice message, the response module 84A then analyzes the semantics of the voice message, finds a response text message adopted to reply to the voice message according to the analysis results, and processes the response text message into an original response voice message. Finally, the original response voice message is sent back to the electronic device 90A via the second wireless communication module 81A. The response receiving unit 35A is used for receiving the original response voice message sent back from the smart voice assistant 80A. The frequency adjustment unit 33A is used for adjusting the frequency of the original response voice message according to the hearing parameter to generate the response voice message.

In the second embodiment of the present invention, the voice message output module 40A is used for outputting the response voice message to the audio processing chip 94A. The response voice message, after the digital/analog conversion processing, can be output by the speaker 95A (i.e. voice playback).

Figure 5:
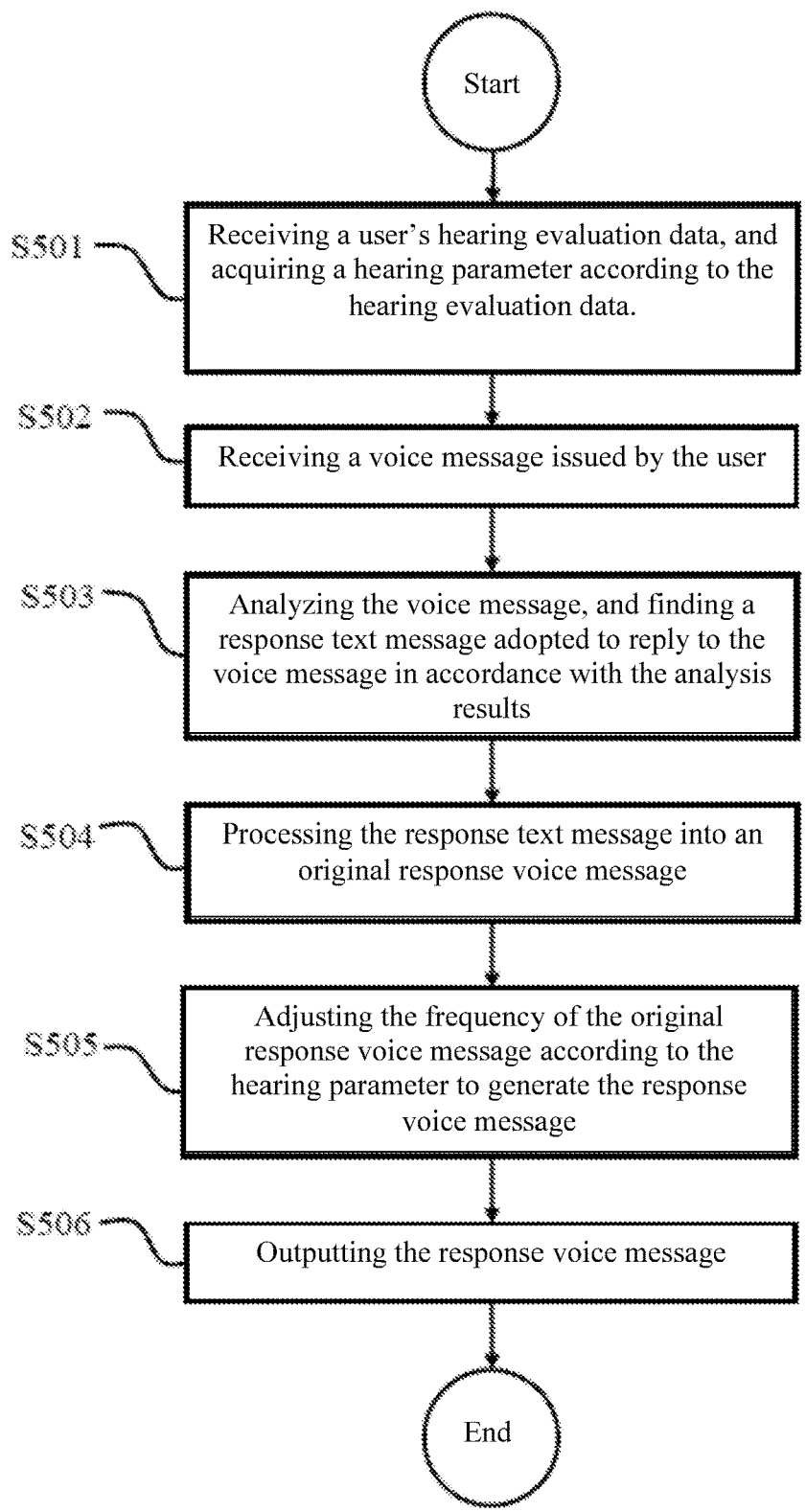
FIG. 5 is a flowchart showing steps of a method of adjusting output voice according to the first embodiment of the present invention.

Then, please refer to FIG. 5 which is a flowchart showing steps of a method of adjusting output voice according to a first embodiment of the present invention. Also refer to FIG. 1.

In the first embodiment of the present invention, the method of adjusting output voice in the present invention is applicable to a smart voice assistant 80 as shown in FIG. 1. Specifically, the steps involved are implemented by the smart voice system 1. The smart voice assistant 80 is connected to the electronic device 90.

As shown in FIG. 1 and FIG. 5, first, in Step S501: Receiving a user's hearing evaluation data, and acquiring a hearing parameter according to the hearing evaluation data.

In the first embodiment of the present invention, the user U can input his/her hearing evaluation data H via the input interface 91 (e.g. a touch screen), including, for example, age information and gender information. The hearing evaluation data H will be sent to the smart voice assistant 80 through the first wireless communication module 92 and received by the second wireless communication module 81. Then, the hearing evaluation data H is sent to the smart voice system 1 through the second wireless communication module 81 and received by the data receiving module 10. After receiving the hearing evaluation data H of the user U, by looking for a relationship table as shown in FIG. 3, the data receiving module 10 further acquires a corresponding hearing parameter according to the hearing evaluation data H, wherein the hearing parameter is the minimum volume data that the user can hear for different frequencies of sound.

In Step S502: Receiving a voice message issued by a user.

After the user U enables the smart voice service function on the electronic device 90, once the user speaks to the electronic device 90 (i.e. a voice message is issued), the issued voice message V will be received by the microphone 93. Then, the voice message V will be sent to the smart voice assistant 80 and received by the second wireless communication module 81. The voice message V will be sent to the smart voice system 1 by the second wireless communication module 81, and will be received by the voice message receiving module 20.

In Step S503: Analyzing the voice message, and finding a response text message adopted to reply to the voice message in accordance with the analysis results.

After the voice message receiving module 20 receives the voice message V, the semantic analysis unit 31 of the voice response module 30 analyzes the semantics of the voice message V, and in accordance with the analysis results, finds a response text message adopted to reply to the voice message V.

In Step S504: Processing the response text message into an original response voice message.

After Step S503 is completed, the voice message generation unit 32 of the voice response module 30 processes the response text message into an original response voice message.

In Step S505: Adjusting the frequency of the original response voice message according to the hearing parameter to generate a response voice message.

Once the response text message is processed into an original response voice message, the frequency adjustment unit 33 of the voice response module 30 then adjusts the frequency of the original response voice message according to a hearing parameter acquired by the data receiving module 10 to generate a response voice message.

It should be noted here that in other embodiments, the voice message generation unit 32 can also directly process the response text message into the response voice message according to a hearing parameter, that is, in the process of performing text-to-speech, adjust the output sound frequency according to the hearing parameter. In other words, a single step: processing the response text message into the response voice message according to the hearing parameter, can be used to replace the Step S504 and S505.

Finally, in Step S506: Outputting the response voice message.

After Step S505 is completed, finally, the voice message output module 40 outputs the response voice message to the second wireless communication module 81, and sends the response voice message to the electronic device 90 via a second wireless communication module 81. The response voice message, after the digital/analog conversion processing of the audio processing chip 94, can be output by the speaker 95 (i.e. voice playback).

Figure 6:
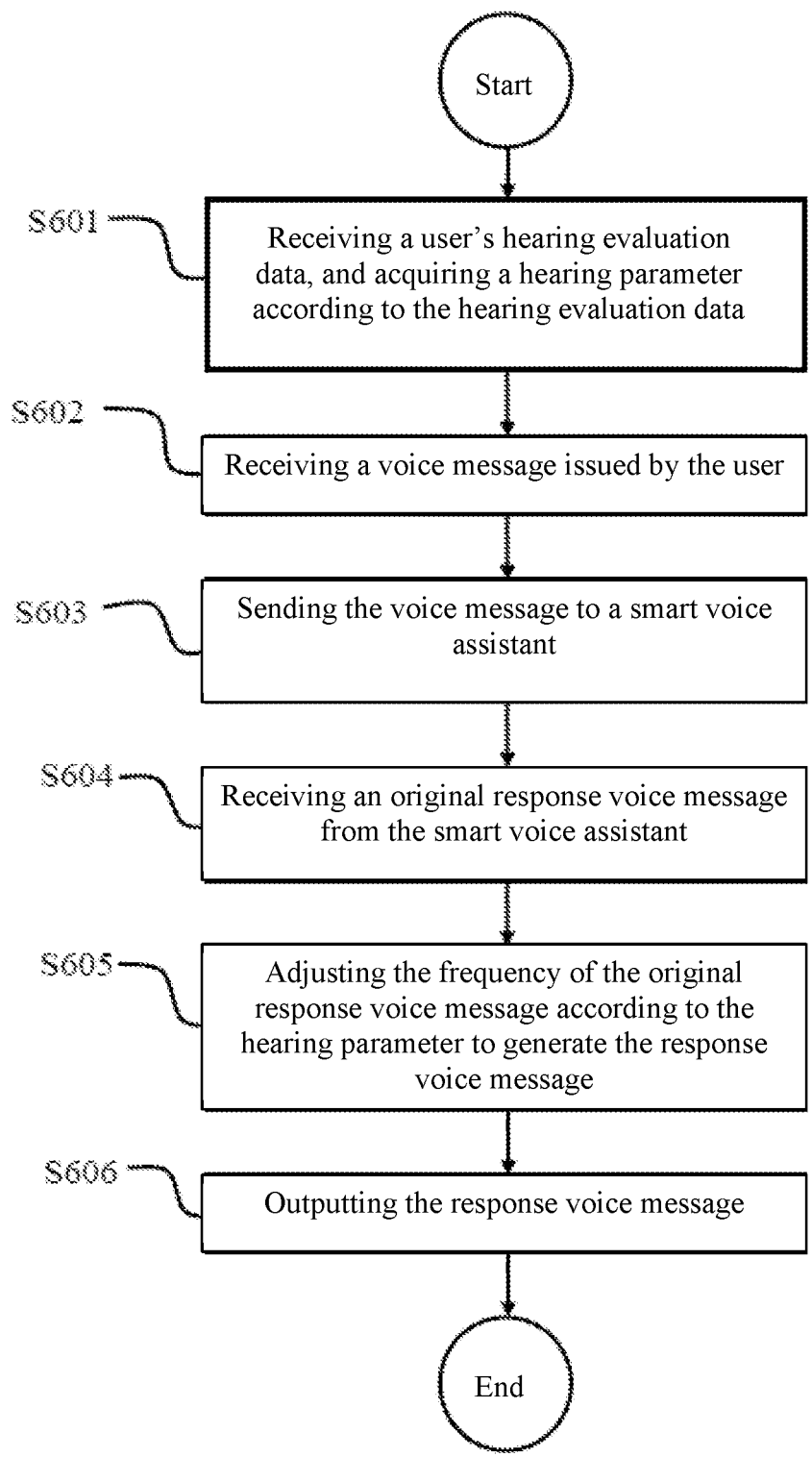
FIG. 6 is a flowchart showing steps of a method of adjusting output voice according to the second embodiment of the present invention.

Finally, please refer to FIG. 6 about a flowchart showing steps of a method of adjusting output voice according to a second embodiment of the present invention. Also refer to FIGS. 2, 3, and 4.

As shown in FIG. 2, in the second embodiment of the present invention, the method of adjusting output voice in the present invention is applicable to, for example, the electronic device 90A as shown in FIG. 2, wherein the steps involved are implemented by smart voice system 1. The electronic device 90A is connected to a smart voice assistant 80A.

As shown in FIG. 6, first, in Step S601: Receiving a user's hearing evaluation data H, and acquiring a hearing parameter according to the hearing evaluation data H.

In the second embodiment of the present invention, similarly, a user can input his/her hearing evaluation data H via the input interface 91A. After receiving the hearing evaluation data H from the input interface 91A, the data receiving module 10A acquires a corresponding hearing parameter according to the hearing evaluation data H, by looking for the corresponding relationship shown in FIG. 3.

In Step S602: Receiving a voice message issued by the user.

Similarly, in the second embodiment of the present invention, after the user U enables the smart voice service function on the electronic device 90, the voice message V sent to the electronic device 90 via the microphone 93A will be transmitted to the audio processing chip 94A for analog/digital conversion processing. The processed voice message V is then sent to the smart voice system 1 and received by the voice message receiving module 20.

In Step S603: Sending the voice message to a smart voice assistant.

After the voice message receiving module 20A receives the voice message V, then, the issuing unit 34A of the voice response module 30A sends the voice message V to the smart voice assistant 80A via the first wireless communication module 92A.

After the second wireless communication module 81A of the smart voice assistant 80A receives the voice message V, the response module 84A then analyzes the semantics of the voice message V, and in accordance with the analysis result, finds a response text message adopted to reply to the voice message V. Then, the response module 84A processes the response text message into an original response voice message, and then sends back the processed original response voice message to the electronic device 90A via the second wireless communication module 81A.

In Step S604: Receiving an original response voice message from the smart voice assistant.

The original response voice message is sent back to the electronic device 90A via the second wireless communication module 81A and then can be received by the response receiving unit 35A of the response module 30A.

In Step S605: Adjusting the frequency of the original response voice message according to the hearing parameter to generate the response voice message.

After receiving the original response voice message from the smart voice assistant 80A, the frequency adjustment unit 33A of the voice response module 30 A, adjusts the frequency of the original response voice message according to the hearing parameter acquired by the data receiving module 10 to generate the response voice message.

Finally, in Step S606: Outputting the response voice message.

After the Step S605 is completed, finally, the voice message output module 40 outputs the response voice message to an audio processing chip 94A. The response voice message after the digital/analog conversion processing of the audio processing chip 94A, can be output by the speaker 95A (i.e. voice issued).

It is known from the preceding disclosure, the method of adjusting output voice disclosed in the present invention can adjust the output sound frequency of the smart voice service function on an electronic device according to a user's hearing status. Therefore, even if the users of the electronic device have hearing obstacles, they still can feel the convenience brought by the smart voice service function on the electronic device.

As described above, the objective, means, and efficiency of the present invention are all different from conventional characteristics in the prior art. It will be appreciated if the committee can review and grant a patent to benefit the society. However, it should be noted that the described embodiments are only for illustrative and exemplary, and that various changes and modifications may be made to the described embodiments without departing from the scope of the invention as disposed by the appended claims.

What is claimed is:
1. A smart voice system, comprising:
 a data receiving module, used for receiving a user's hearing evaluation data, and acquiring a user's hearing parameter according to the hearing evaluation data, wherein the user's hearing parameter comprises, for each of a plurality of different frequencies of sound, a minimum volume data that the user can hear for each different frequencies of sound;

a voice message receiving module, which is used for receiving a voice message issued by the user;

a voice response module comprising:

an issuing unit, which is used for sending the voice message to a voice server to generate an original response voice message after the voice server analyzes the voice message;

a response receiving unit, which is used for receiving the original response voice message from the voice server;

a frequency adjustment unit, which is used for adjusting a frequency of the original response voice message according to the user's hearing parameter to generate a response voice message based on the user's hearing parameter; and a voice message output module, which is used for outputting the response voice message.

2. The smart voice system as claimed in claim 1, wherein the voice response module comprising:

a semantic analysis unit, which is used for analyzing the voice message, and searching for a response text message adapted to reply to the voice message based on an analysis result; and a voice message generation unit, which is used for processing the response text message into the response voice message according to the user's hearing parameter.

3. The smart voice system as claimed in claim 1, wherein the voice response module comprising:

a semantic analysis unit, which is used for analyzing the voice message, and searching for a response text message adapted to reply to the voice message based on an analysis result;

a voice message generation unit, which is used for processing the response text message into an original response voice message; and a frequency adjustment unit, which is used for adjusting a frequency of the original response voice message according to the user's hearing parameter to generate the response voice message.

4. The smart voice system as claimed in claim 1, wherein the user's hearing evaluation data includes age information and/or gender information.

5. A method of adjusting output voice applicable to a voice server, wherein the voice server is connected to an electronic device, the method of adjusting output voice comprising the steps of:

receiving a user's hearing evaluation data, and acquiring a user's hearing parameter according to the hearing evaluation data, wherein the user's hearing parameter comprises, for each of a plurality of different frequencies of sound, a minimum volume data that the user can hear for each different frequencies of sound;

receiving a voice message issued by the user;

analyzing the voice message, and searching for a response text message adapted to reply to the voice message based on an analysis result of the voice message analysis;

processing the response text message into an original response voice message from the voice server;

adjusting a frequency of the original response voice message according to the user's hearing parameter to generate a response voice message based on the user's hearing parameter; and outputting the response voice message.

6. The method of adjusting output voice as claimed in claim 5, wherein the step of generating the response voice message according to the response text message comprising:

processing the response text message into the response voice message according to the user's hearing parameter.

7. The method of adjusting output voice as claimed in claim 5, wherein the user's hearing evaluation data includes age information and/or gender information.

8. A method of adjusting output voice applicable to an electronic device, wherein the electronic device is connected to a voice server, the method comprising the steps of:

receiving a user's hearing evaluation data, and acquiring a user's hearing parameter according to the hearing evaluation data, wherein the user's hearing parameter comprises, for each of a plurality of different frequencies of sound, a minimum volume data that the user can hear for each different frequencies of sound;

receiving a voice message issued by the user;

sending the voice message to the voice server;

receiving an original response voice message from the voice server, wherein the original response voice message is acquired by the voice server according to the voice message;

adjusting a frequency of the original response voice message according to the user's hearing parameter to generate a response voice message based on the user's hearing parameter; and outputting the response voice message.

9. The method of adjusting output voice as claimed in claim 8, wherein the user's hearing evaluation data includes age information and/or gender information.

* * * * *